United States Patent
Lazaro Gomez

Patent Number: 6,049,382
Date of Patent: Apr. 11, 2000

[54] APPARATUS AND PROCEDURE FOR CHARACTERIZATION OF SPRAYS COMPOSED BY SPHERICAL PARTICLES

[75] Inventor: Benigno Lazaro Gomez, Madrid, Spain

[73] Assignee: Sener, Ingenieria y Sistemas, S.A., Spain

[21] Appl. No.: 09/165,986

[22] Filed: Oct. 2, 1998

[30] Foreign Application Priority Data

Oct. 3, 1997 [ES] Spain ................................ 9702073

[51] Int. Cl.⁷ .................................................. G01N 15/02
[52] U.S. Cl. ........................................... 356/336; 356/326
[58] Field of Search ................................... 356/336, 337, 356/338, 339, 341, 343, 319, 326

[56] References Cited

U.S. PATENT DOCUMENTS

| | | | |
|---|---|---|---|
| 4,095,775 | 6/1978 | Hotham | 356/102 |
| 4,329,054 | 5/1982 | Bachalo | 356/336 |
| 4,387,993 | 6/1983 | Adrian | 356/336 |
| 4,492,467 | 1/1985 | Drain et al. | 356/336 |
| 4,537,507 | 8/1985 | Hess | 356/336 |
| 4,540,283 | 9/1985 | Bachalo | 356/336 |
| 4,986,659 | 1/1991 | Bachalo | 356/336 |
| 5,654,797 | 8/1997 | Moreau et al. | 356/336 |

FOREIGN PATENT DOCUMENTS

| | | |
|---|---|---|
| 19525847 | 1/1997 | Germany . |
| 2204678 | 11/1988 | United Kingdom . |
| 8404592 | 11/1984 | WIPO . |

Primary Examiner—Frank G. Font
Assistant Examiner—Layla Lauchman
Attorney, Agent, or Firm—Ostrolenk, Faber, Gerb & Soffen, LLP

[57] ABSTRACT

An apparatus and procedure is described for the characterization of sprays composed by spherical particles, by means of a laser source (1) generating a collimated laser beam (2) that is passed through the spray to be characterized. The laser beam is made to coincide with the x-axis of a cartesian coordinate system (3) contained in a measurement plane perpendicular to the spray axis. A scattering collection means (5) is disposed to obtain the 90° scattering activity produced by the spray material in a small probe volume formed at the intersection of the laser beam and the object volume of the scattering collection means. Additional collection means (14) are included to obtain the attenuation of the laser beam passing trough the measurement plane. The optical systems (5 and 14) are coupled to photodetectors (10 and 18) and signal processing units (10' and 18') able to generate electrical signals proportional to the received light intensities. A transverse means is also disposed to move the spray along the laser beam direction and perpendicular to it as to sequentially obtain a tomographic record of the scattering and attenuation activity in points of the spray forming a Cartesian grid within the measurement plane. Concentration measuring means (21) are coupled to the attenuation and scattering electrical signals output to extract the information related to the number density of the spray in the nodes of the tomographic grid system.

25 Claims, 4 Drawing Sheets

APPARATUS AND PROCEDURE FOR CHARACTERIZATION OF SPRAYS COMPOSED BY SPHERICAL PARTICLES

BACKGROUND OF THE INVENTION

The present invention relates to a procedure for characterizing a spray composed of spherical particles, by determining information related to its number density (particles per unit volume) in points located within a measurement plane intersected by the spray. The characterization is based on the scattering of a laser light beam by the particles contained in the spray, when the particle size is large enough for the Mie scattering theory to apply. The invention includes also the apparatus to materialize the procedure.

There are a number of techniques which, working in the Mie regime, exploit the scattering of laser light by a spray of particles to extract information related to the spray number density.

A technique known as laser diffraction particle sizing determines the spatial number size distribution of the spray material intersected by a laser beam by measuring the forward scattering pattern through a set of photodetectors located in the focal plane of a receiving lens. The application of this technique for characterizing sprays is used in the apparatus developed by the British company Malvern Instruments, where the photodetectors are ring-shaped photodiodes. Diffraction is the dominant scattering mode in the collection angles sensed by the photodiodes. Since the far field diffraction pattern for spherical particles is a well known function of the particle size and the laser wavelength, the technique obtains the size distribution by matching the measured diffraction pattern to that obtained from a collection of particles distributed in a finite number of size classes. In addition, the attenuated laser intensity is measured with a photodiode located in the receiving lens axis. Knowing the attenuation of the laser beam and the spray size distribution allows the technique to infer the spray number density. Since the technique is an on-axis method, the laser diffraction technique can only give a measure of the spray number density averaged along the volume intercepted by the spray and the laser beam.

Another family of methods developed to obtain information related to the spray number density is based on counting techniques initially used for fluid anemometry purposes. The optical arrangement is similar to that of the dual beam laser Doppler velocimetry system (LDV). The interference pattern formed at the intersection of two coherent laser beams modulates the light scattered by particles passing through the probe volume. A set of photodetectors is placed to detect the off-axis particle scattering activity. The velocity of the particles can be obtained by recording the Doppler frequency of the scattering light produced by the particles intersecting the probe volume. The size of the particles can be inferred either from a measurement of the visibility of the Doppler signal (technique disclosed in U.S. Pat. No. 4,329,054), or from the phase difference of the Doppler signal detected in spatially separated photodetectors (technique disclosed, under different hardware implementations, in International Patent WO 84/04592 and in U.S. Pat. No. 4,540,283). A critical aspect of the obtained size distribution is that it is biased towards the large particle sizes, since the laser beams have a gaussian intensity decay from their axis, and the large particles scatter more light intensity than the smaller ones. As a consequence, the characteristic probe volume of the large particles is greater than that of the smaller ones. A deconvolution based on the statistics of the transit time and velocity of the particles can be applied to eliminate this bias. The velocity of the particles also biases the number-size distribution but, since this velocity is known, a transformation can be introduced to obtain the unbiased spatial number-size distribution. The number density information can be obtained by knowing the cross-stream area of the formed probe volume and the number of particles passing through it during a known measurement time. Being based on off-axis scattering analysis, these counting techniques can perform highly spatially resolved number density measurement. Determination of the probe volume cross-stream area and of the effective measurement time encounters, however, severe difficulties when characterizing sprays subjected to high optical attenuation levels and/or flowing in directions other than that perpendicular to the laser beams bisector.

The invention disclosed hereinafter performs spatially resolved measurements of a quantity proportional to the spray number density in a measurement plane intersected by the spray and characterized by arbitrarily large optical attenuation levels, and arbitrary spray trajectory angles. In addition, the technique of the invention can be combined with independently obtained measurement of the spray number-size histogram and of the velocity-size correlation to explicitly infer the spray number density and volume flux without knowledge of the probe volume cross-stream area or of the effective measurement time.

SUMMARY OF THE INVENTION

An apparatus and procedure is described to obtain information related to the concentration of a polydispersed spray of spheres (referred hereinafter as particles), having optical attenuation levels arbitrary large but lower than 100%. Specifically, the apparatus and procedure is able to determine spatially resolved information proportional to the spray number density (particles per unit volume) in a measurement plane intersecting the spray. In addition, and combining this result with an independent measurement of the spray spatial diameter and velocity distribution, the apparatus and procedure can be used to generate tomographic maps of the spray volume flux (volume of particles per unit time per unit surface). The apparatus and procedure principle of operation is based on the analysis of light scattered by the particles. The procedure includes means to extract the number density related information in sprays characterized by arbitrary, lower than 100%, optical attenuation levels along directions embedded in the measurement plane. A laser generating means is provided to generate a collimated light source. The laser beam is passed through the measurement plane. A scattering collection means is disposed to obtain the 90° scattering activity produced by the spray material in a small probe volume formed at the intersection of the laser beam and the object volume of the scattering collection means. An additional collection means is included to obtain the attenuation of the laser beam passing trough the measurement plane. The scattering and attenuation collection means are directed to photodetectors and signal processing means to obtain electrical signals proportional to the scattered and attenuated light intensities. A transverse means is disposed to move the spray along the laser beam direction and perpendicular to it as to sequentially obtain a tomographic record of the scattering and attenuation activity in points of the spray forming a cartesian grid within the measurement plane. Concentration measuring means are coupled to the tomographic attenuation and scattering electrical signals to extract the information related to the number density of the spray in the nodes of the tomographic grid system.

DESCRIPTION OF DRAWINGS

The invention will be discussed making reference to a set of figures attached at the end of the document, in which.

DETAILED DESCRIPTION OF THE INVENTION

Figure 1:
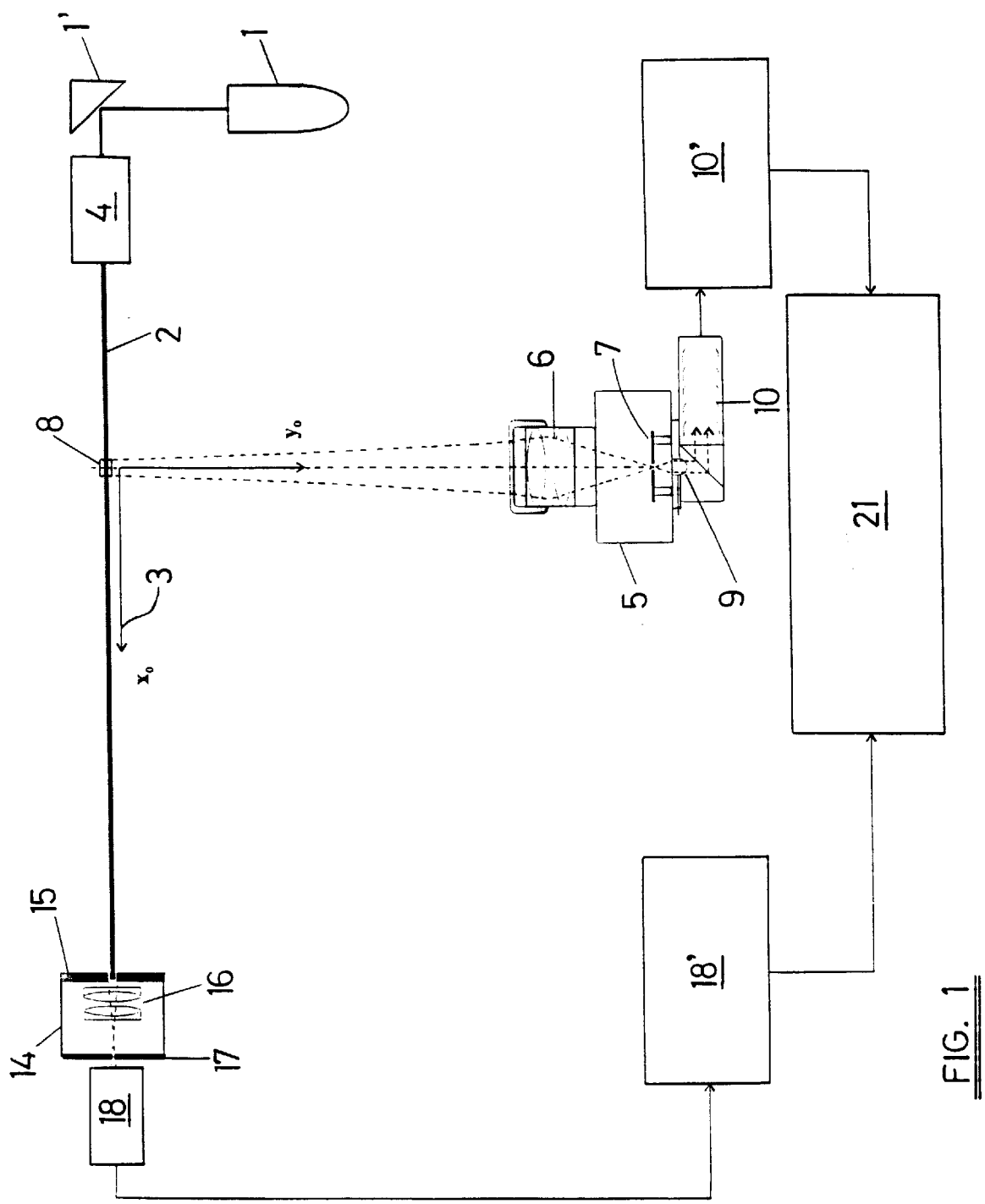
FIG. 1 schematically describes the preferred physical embodiment of the invention.

An apparatus and procedure to extract information related to the particle number density of polydispersed sprays using laser scattering techniques operating in the Mie regime is presented. The apparatus and procedure are able to generate the number density information corresponding to a spray composed by spherical particles in points located within a plane intersected by the spray. FIG. 1 displays the physical arrangement of the optical parts used in the apparatus.

Figure 2:
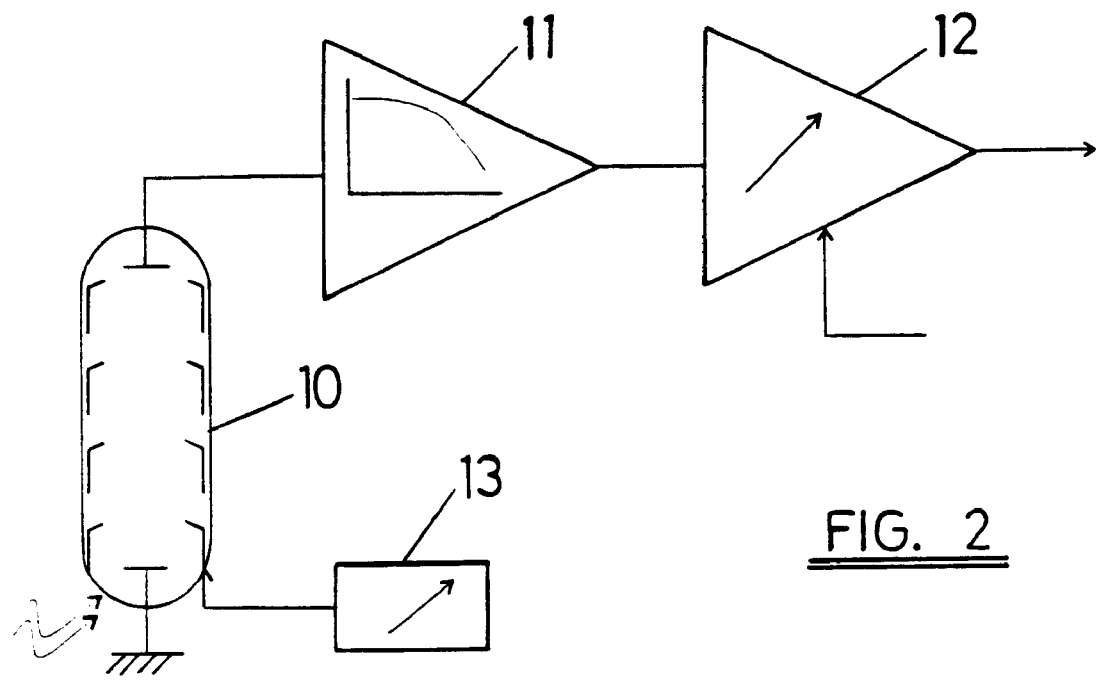
FIG. 2 schematically presents the scattering signal processing means.
Figure 3:
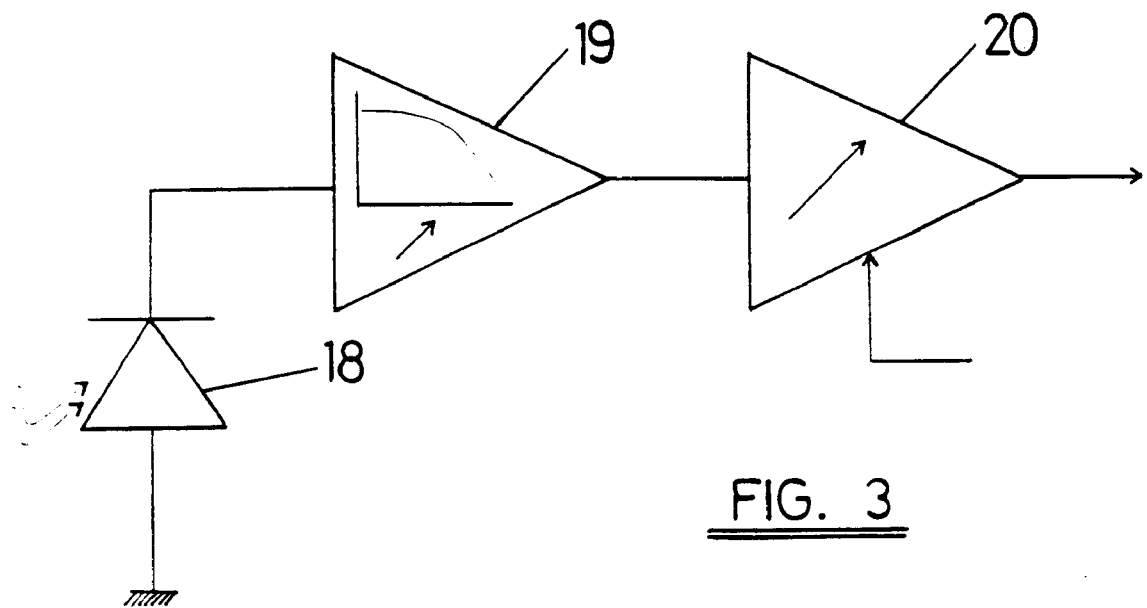
FIG. 3 schematically presents the attenuation signal processing means.

A laser head 1 generates a collimated, visible laser beam 2, which is directed (by means, for example, of an optical element 1') through the axis of a cartesian measurement system 3 ($x_0$, $y_0$). This system is affixed to the optical elements to facilitate the geometrical description of the optical arrangement. A beam expander unit 4 ensures an output beam with a characteristic diameter much greater than the maximum size of the particles to be characterized. The plane formed by the cartesian coordinate system 3 will be referred to as the measurement plane. The laser beam propagates along the $x_0$ direction of the optics coordinate system 3, and is linearly polarized along the $x_0$–$z_0$ plane, with $z_0$ being aligned along the measurement plane normal direction. A scattering activity collection means 5 is located with its optical axis at 90° of the laser propagation direction. The $y_0$ axis coincides with the optical axis of scattering activity collection means. The scattering activity collection means are composed by a small depth of field, moderate f number entrance optics, 6, and a rectangular pinhole 7 located in the image plane of the entrance optics. The rectangular pinhole images a probe volume 8 centered at the origin of the coordinate system 3. The geometry of the scattering pinhole 7 is such that the probe volume dimensions along the $x_0$ and $z_0$ directions are much larger than the maximum particle size to be characterized, but smaller than the characteristic diameter of the laser beam 2. The light passing through the scattering pinhole 7 is collimated by an output lens 9 and directed to a photodetector 10. The electrical current generated by the photodetector is then handled by scattering signal processing means 10', shown in FIG. 2. The scattering signal processing means amplifies the scattering current produced by photodetector 10 through a low-pass filtered input amplifier 11 and a variable gain output amplifier 12 with zeroing output capability. A variable high voltage power supply unit 13 controls the sensitivity of the scattering photodetector 10. The laser beam intensity that is not attenuated by the spray material intersecting the $x_0$–$y_0$ plane is directed to attenuation collection means 14 (FIG. 1). The axis of the attenuation collection means is coincident with the $x_0$ axis of the coordinate system 3. The laser radiation reaching the attenuation collection means 14 passes through an entrance aperture 15 whose diameter is similar to the laser beam characteristic diameter, and is focused by a high f number receiving lens system 16. A small, circular pinhole 17 is located in the focal plane of the attenuation collection means receiving lens system 16. The receiving lens/pinhole combination 16–17 is such as to reject optical radiation whose propagation direction differs more than an angle of the order of 1 mrad from the attenuation collection means axis. The radiation passing through the attenuation collection means pinhole 17 is directed to a photodetector 18. The electrical current generated by the photodetector is then handled by attenuation signal processing means 18', shown in FIG. 3. The attenuation processing means amplify the electrical current produced by photodetector 18 through a variable gain, low-pass filter input amplifier 19, and a variable gain output amplifier 20 with zeroing output capability.

Finally, the electrical signals related to the scattering and attenuation activity are converted, by post-processing means 21 in a measure of the spray particle density times the square of the spray mean quadratic diameter that is present in each point of the measurement grid.

The measurement principle of the apparatus schematically shown in FIG. 1 is based on the fact that, under proper conditions, the scattering radiation sensed by sensor 10 is proportional to the number density $N_D$ (particles per unit volume) multiplied by the square of the spray mean quadratic diameter $D_{20}$ characterizing the material located in the probe volume:

$$w_{sc} \propto N_D D_{20}{}^2 = N_D \int n_s(D) D^2 dD. \qquad (1)$$

where $w_{sc}$ and $D_{20}$ denote the light power scattered by the particles intersecting the probe volume 8 which propagates towards photodetector 10, and the spray average diameter constructed from the second moment of the spatial number-size probability density function $n_s(D)$ respectively. Expression (1) assumes that the particles are illuminated by plane wave light radiation with uniform intensity along distances of the order of the particle sizes D. The error incurred when using expression (1) can be estimated by using the generalized Lorenz-Mie theory of scattering. Use of it allows one to obtain the light radiation scattered by spheres of given index of refraction and that is collected within a solid angle similar to that subtended by the scattering collection means 5.

Figure 4:
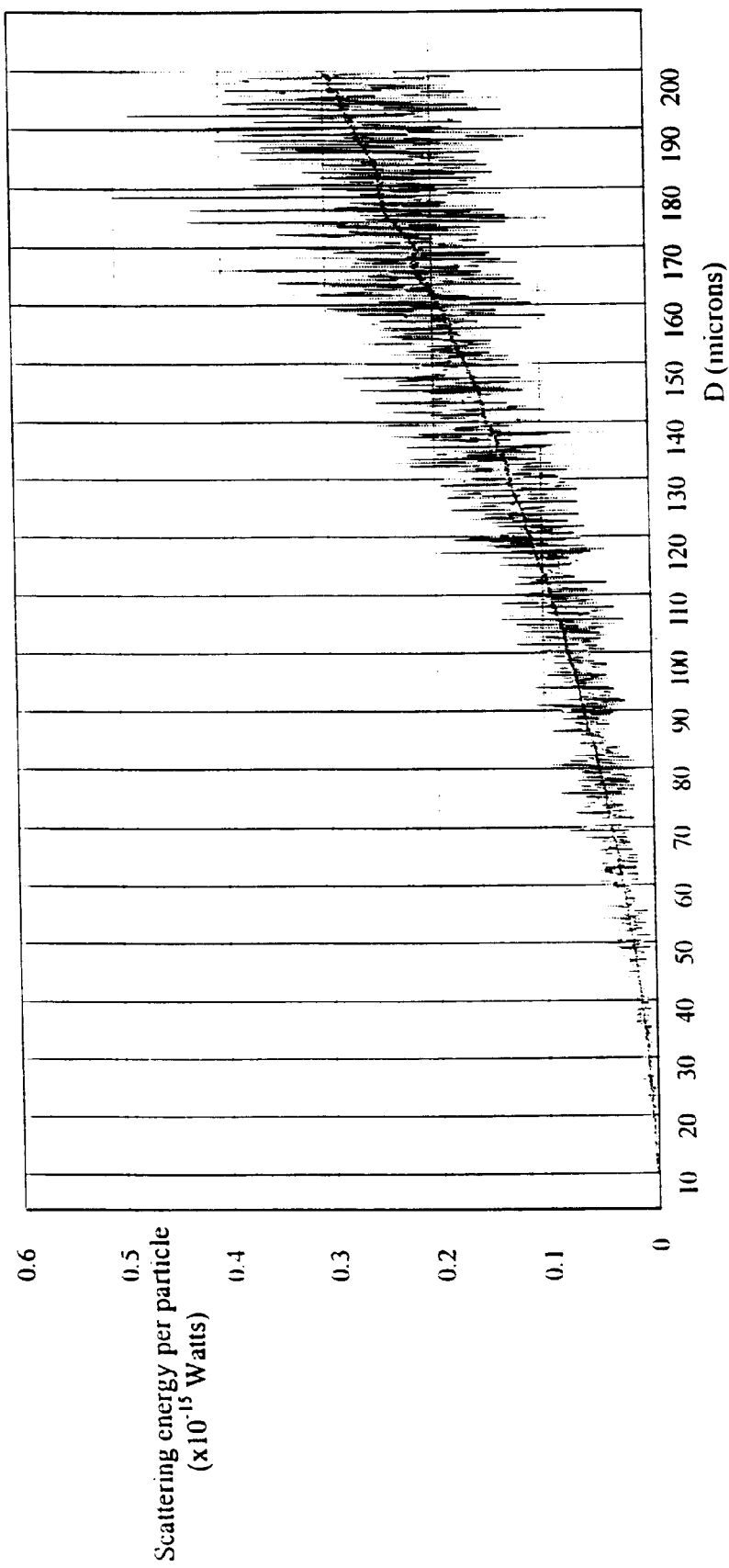
FIG. 4 displays the light intensity received by the scattering collection means for arbitrary, spherical particles located in the probe volume.

The result of applying the Lorenz-Mie theory to a single sphere is shown in FIG. 4, which displays the scattered light power for individual particles of given diameter and refraction index m=1.33, and after filtering out the original data on size bins with a 5 $\mu$m width. The results presented in FIG. 4 correspond to an incident laser radiation characterized by a power density of $10^3$ W/m$^2$ and a $\lambda$=0.51 $\mu$m wavelength, matching the blue line of an Argon-Ion laser. FIG. 4 shows the size to size large scattering power variations that are obtained when considering particles of fixed diameter. These power excursions are due to superficial wave interference effects. However, when the average power corresponding to a given, 5 $\mu$m wide, size interval is obtained, the excursions are highly damped. In this case, proportionality of the scattered power to the square of the diameter located at the center of the size interval is obtained within a given accuracy for particles satisfying the geometrical optics condition:

$$q = 2\pi(\text{Re}(m) - 1)\frac{D}{\lambda} \gg 1, \quad (2)$$

with Re(m) being the real part of the index of refraction m. Thus, for 5 $\mu$m size width families, the points in the smoothed curve of FIG. 4 separate less than 2% from a fitting parabola for q>20 (i.e. D>5 $\mu$m).

When a polydispersed spray is considered, and if independent scattering conditions apply, the power scattered from the probe volume must be multiplied by the number of particles embedded on it, i.e., by the spray number density times the volume of the probe region. Thus, expression (1) is recovered. The condition under which independent scattering occurs is that the particles are separated more than 2 diameters. This restriction establishes a limit for which expression (1) still holds:

$$N_D \leq 0.01 D_{10}^{-3}, \quad (3)$$

with $D_{10}$ being the spray average diameter constructed from the first moment of the spatial probability density function. Condition (3) is satisfied except for extremely high particles packing.

Figure 5:
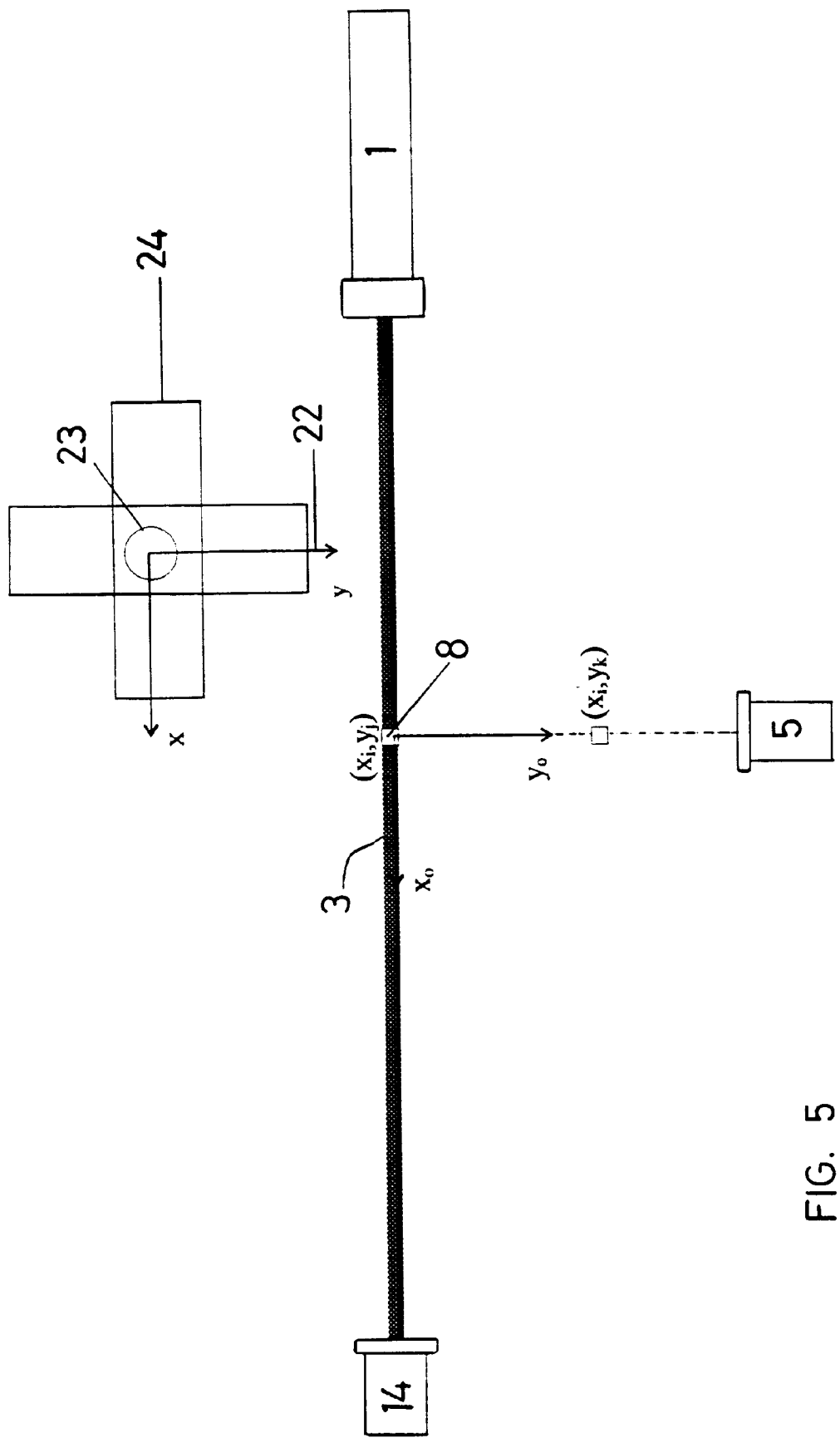
FIG. 5 schematically presents the preferred physical embodiment used in the tomographic measurements.

The procedure to extract the information related to the spray number density makes use of FIG. 5, which schematically displays the arrangement of the apparatus presented in FIG. 1. The coordinate system 22, (x,y), is parallel to the optics related coordinate system 3, ($x_0$, $y_0$), and is fixed to the spray produced by injector 23. The two-axis transverse 24, rigidly attached to the spray nozzle 23, is used to move around coordinate system 22 with respect to coordinate system 3. The spray nozzle 23 is located at some distance $z_N$ from the measurement plane formed by the coordinate system 3. The apparatus of FIG. 1 with the set-up presented in FIG. 5 is used to record the scattering activity of the particles created by the spray nozzle 23 as they intersect the measurement plane formed by coordinate system 3. The characterization proceeds by using the two-axis transverse 24 to sequentially position a set of points ($x_i$,$y_j$), related to the spray coordinate system 22, at the probe volume location 8, and recording the signals produced by the attenuation and scattering collection means. It will be assumed for simplicity that the grid system formed by the set ($x_i$,$y_j$) has constant separation $\Delta x$, $\Delta y$ in the two cartesian coordinate directions, and covers a rectangular domain composed by $N_x$, $N_y$ lines in the x, y direction. Extension of the procedure for non-uniform grid spacing is straightforward.

Denoting ($x_i$, $y_j$) as an arbitrary point of the spray grid that is positioned at the probe volume location 8, and ($x_j$,$y_k$) as an arbitrary point of the spray which, in these measurement conditions, is located along the axis of the scattering collection means, use will be made of the following notation:

$w_1(x_i,y_j)$: Laser power available at the probe volume 8 which is sensed by the attenuation collection means.

$w_2(x_i,y_j)$: Laser power available at the probe volume 8 which is sensed by the scattering collection means.

$w_{sc}(x_i,y_j,y_k)$, which will be ultimately sensed by the scattering collection means.

Making use of this notation, the undisturbed laser power in characterization line j is $w_1(1,y_j)$; the power laser measured by the attenuation collection means is $w_1(N_x,y_j)$; and the scattering activity measured by the scattering collection means is $w_{sc}(x_i,y_j,N_y)$.

The following set of difference equations is used to describe the evolution of the quantities introduced above:

$$\Delta w_1(x_i, y_j) = -\frac{\pi}{2} N_D D_{20}^2 \Delta x w_1 \Big|_{(x_i,y_j)} \quad (4.1)$$

$$\Delta w_2(x_i, y_j) = -\frac{\pi}{4} N_D D_{20}^2 \Delta x w_2 \Big|_{(x_i,y_j)} \quad (4.2)$$

$$-\Delta w_2(x_i, y_j) = \frac{\Delta x}{K} w_{sc}(x_i, y_j, y_j) \quad (4.3)$$

$$w_1(1, y_j) = w_2(1, y_j) = w_{10} \quad (4.4)$$

The above set implies:
a) The particle scattering process can be evaluated by the geometrical optics approximation.
b) The attenuation sensor senses only the attenuated radiation. It rejects the forward diffraction lobe and the large angle portions of the spray scattering.
c) The scattering sensor senses the original attenuated radiation and the portion of the scattering included in the forward diffraction lobe.
d) The radiation reaching the scattering sensor means is a fraction of the large angle scattering by the particles present in the probe volume.

Constraint (2) and the polydispersed character of the sprays being evaluated support assumption a). Assumptions b) and c) can be supported, to given accuracy, by proper design of the attenuation and scattering collection means. Finally, assumption d) reverts to expression (1) by establishing the proportionality between the reduction in $w_2$ and the cause creating such reduction, i.e., the large angle scattering.

Manipulation of equations (4.1) to (4.4) leads to:

$$N_D D_{20}^2 \Big|_{x_i,y_j} = \frac{4}{\pi}\frac{1}{K} = \frac{w_{sc}(x_i, y_j, y_j)/w_{10}}{1 - \frac{1}{K}\displaystyle\sum_{x_k=x_i}^{x_k=x_i-1}\frac{w_{sc}(x_k, y_j, y_j)}{w_{10}}\Delta x}. \quad (5)$$

The scattering proportionality constant K can be obtained from the attenuation level and scattering profile recorded at an arbitrary, j=constant line, y=$y_j$:

$$K_j = \frac{\displaystyle\sum_{x_k=x_i}^{x_k=x_{Nx}} \frac{w_{sc}(x_k, y_j, y_j)}{w_{10}}\Delta x}{1 - w_1(x_{N_x}, y_j)/w_{10}}, \quad (6)$$

where the quantity $w_1(x_{Nx},y_j)/w_{10}$ represents the signal registered by the attenuation collection means with spray being present divided by the signal registered when no spray is present along the laser propagation path. In the limit expressed by inequality (2), the constant $K_j$ should be independent of the characterization line j.

The light intensities $w_{sc}(x_i,y_j,y_j)$ must be related to the ones registered by the scattering collection means $w_{sc}(x_i,y_j,y_{Ny})$ by an additional difference evolution equation:

$$\Delta w_{sc}(x_i, y_j, y_k) = \quad (7)$$

$$\begin{cases} 0 & , y_k - y_j \leq L_{sc} \\ -\frac{\pi}{4} N_D D_{20}^2\Big|_{(x_i,y_k)} w_{sc}(x_i, y_j, y_k)\Delta y & , y_k - y_j > L_{sc} \end{cases}$$

with $L_{sc}$ being related to the scattering collection means depth of field. Expression (7) establishes that the radiation scattered at the probe volume its attenuated only by the large angle scattering mechanism as it travels towards the scattering collection means 5. This assertion can be supported to given accuracy by proper design of the scattering collection means. Using equation (7) it is possible to establish a relationship between $w_{sc}(x_i, y_j, y_j)$ and $w_{sc}(x_i, y_j, y_{Ny})$:

$$\frac{w_{sc}(x_i, y_j, y_i)}{w_{10}} = C_{RX}(x_i, y_j) \cdot \frac{w_{sc}(x_i, y_j, y_{xy})}{w_{10}}. \tag{8.1}$$

where the reception correction coefficient $C_{RX}(x_i, y_j)$ is given by:

$$C_{RX}(x_i, y_j) = \prod_{y_k=y_{Ny}}^{y_k=y_i+L_{sc}} \left(1 + \frac{\pi}{4} N_D D_{20}^2 \Delta y_{(x_i, y'_k)}\right), \; C_{RX}(x_i, y_{Ny}) = 1. \tag{8.2}$$

Determination of the coefficient $C_{RX}(x_i, y_j)$ requires, therefore, knowledge of $N_D D_{20}^2$ along the lines $y_k, y_k > y_j$.

A procedure can then be constructed to obtain the measurement of $N_D D_{20}^2$ along a discrete grid system of points $(x_i, y_j)$ distributed in the measurement plane:

1) Guess a value of the scattering constant by averaging expression (6) over a set of $y_j$ lines in a spray region where the light power measured by the scattering collection means $w_{sc}(x_i, y_j, y_{Ny})$ does not differ substantially from the one that would be measured if no spray was intercepting the propagation of light scattered at the probe volume until it reaches the scattering collection means:

$$\tilde{K} = \frac{1}{N_K} \sum_{j=kI}^{j=kI+N_k} K_j = \frac{1}{N_K} \sum_{j=kI}^{j=kI+N_k} \left( \frac{\sum_{x_k=x_1}^{x_k=x_{Nx}} \frac{w_{sc}(x_k, y_j, y_{Ny})}{w_{10}} \Delta x}{1 - \overline{w_1(x_{Nx}, y_j)}/w_{10}} \right) \tag{9}$$

where the averaging process is applied to $N_k$ number of y-constant lines.

2) Obtain an estimate of the $N_D D_{20(x_i,y_j)}^2$ surface. Resolve the tomographic problem by advancing backwards through the $y_j$ lines, starting from $y_{Ny}$. Use expression (8.2) to obtain first the set of $C_{RX}(x_i, y_j)$ coefficients in the line $y_j$. Obtain then $w_{sc}(x_i, y_j, y_j)/w_{10}$ from the signal recorded by the scattering sensor means $w_{sc}(x_i, y_j, y_{Ny})/w_{10}$ by using expression (8.1). Determine then $N_D D_{20(x_i,y_j)}^2$ from expression (5). Proceed afterwards to the line $y_{j-1}$ until the total tomography is resolved.

3) Determine an updated, more accurate value of the average scattering constant $\tilde{K}$, by inserting in expression (6) the non-dimensional powers $w_{sc}(x_i, y_j, y_j)/w_{10}$ as obtained in the previous step:

$$\tilde{K} = \frac{1}{N_K} \sum_{j=kI}^{j=kI+N_k} K_j = \frac{1}{N_K} \sum_{j=kI}^{j=kI+N_k} \left( \frac{\sum_{x_k=x_1}^{x_k=x_{Nx}} \frac{w_{sc}(x_k, y_j, y_j)}{w_{10}} \Delta x}{1 - \overline{w_1(x_{Nx}, y_j)}/w_{10}} \right) \tag{10}$$

4) Repeat steps 2) and 3) until the updated value of $\tilde{K}$ does not change by a prescribed percentage.

Once that the tomographic measurement $N_D D_{20(x_i,y_j)}^2$ is completed, the volume flux produced by the spray nozzle which intercepts the measurement plane can be obtained if a tomographic measurement of the spatial number-size distribution histogram $n_s(D_k)$ and of the size-velocity correlation $u(D_k)$ are determined by some independent technique. In these quantities, $D_k$ denotes the particle diameter characterizing an arbitrary size bin k in which the particles of the polydispersed spray are classified, whereas $u(D_k)$ is the mean velocity in the direction normal to the measurement plane of the particles contained in size bin k. These two statistical spray magnitudes can be used to obtain a tomographic map of the following velocity-size moment:

$$\overline{DU}_{(x_i,y_j)} = \frac{\sum_k n_s(D_k) D_k^3 u(D_k)}{\sum_k n_s(D_k) D_k^2} (x_i, y_j). \tag{11}$$

The volume flux at point $(x_i, y_j)$ can then be obtained combining the above given velocity-size moment and the $N_D D_{20(x_i,y_j)}^2$ measurement:

$$q(x_i, y_j) = \frac{\pi}{6} N_D \sum_k n_s(D_k) D_{k(x_i,y_j)}^3 = \frac{\pi}{6}(N_D D_{20}^2) \cdot \overline{DU}_{(x_i,y_j)} \tag{12}$$

The apparatus and procedure to obtain a tomographic measurement of the quantity $N_D D_{20}^2$ (number density times square of the average diameter based on the second order moment of the spatial probability density function) and of the volume flux for a spray of particles intersecting a measurement plane with an arbitrary large but lower than 100% attenuation level has been described.

What is claimed is:

1. A method for characterizing a spray made of spherical particles, said method comprising:

providing a laser beam which is made to coincide with an axis of a cartesian coordinate system contained in a measurement plane perpendicular to a spray axis;

recording, with a first optical system, scattering activity generated by the particles that are located at the intersection of the laser beam and an object volume of the first optical system, the first optical system being disposed at an angle which forms approximately a 90° angle with respect to a laser beam propagation direction;

recording, with a second optical system, the optical attenuation suffered by the laser beam after passing through the measurement plane;

coupling the optical systems to photodetectors and a signal processor;

generating electrical signals proportional to the scattering activity and optical attenuation, the generating being performed by the signal processor;

processing the electrical signals to obtain a tomographic map of the magnitude $N_D D_{20}^2$, where $N_D$ is a spray particle density of the spray and $D_{20}^2$ is the square of the spray average quadratic diameter of the spray.

2. The method as claimed in claim 1 where a first estimation of an average scattering constant $\tilde{K}$ which is used to calculate $N_D D_{20}^2$, is obtained through the following expression:

$$\tilde{K} = \frac{1}{N_K} \sum_{j=kl}^{j=kl+N_K} K_j, \quad K_j = \frac{\sum_{x_k=x_1}^{x_k=x_{N_x}} \frac{w_{sc}(x_k, y_j, y_{N_y})}{w_{10}} \Delta x}{1 - w_1(x_{N_x}, y_j)/w_{10}}$$

applied to a number, satisfying $N_K$ ($1 \leq N_K \leq N_y$) of measurement y-profiles obtained in locations $y_{k1}$ to $Yk1+N_k$ of the coordinate system contained in the measurement plane where:

k1 is an integer, satisfying $1 \leq k1 \leq N_y - N_K$, that defines the first measurement y-profile used to compute the estimation of the scattering constant $\underline{K}$;

$N_y$ is the number of y-profiles where the spray characterization is conducted along the y axis of the measurement plane;

$N_x$ is the number of measurement points where the spray characterization is conducted in the x axis of the measurement plane for a specific y-profile;

$y_j$ satisfies $1 \leq j \leq N_y$ and are the locations distributed along the y axis of the measurement plane where the spray characterization y-profiles are conducted, with $y_{N_y}$ being the location of the y-profile closest to the first optical system;

$x_k$ satisfies $1 \leq k \leq N_x$ and are the locations distributed along the x axis of the measurement plane where the spray characterization for each y-profile are conducted, with $x_{N_x}$ being the x-measurement location closest to the second optical system;

$\Delta x$ if the distance between two consecutive locations along the x-axis;

$w_{sc}(x_k, y_j, y_{N_y})$ is the time-averaged laser power scattered by the particles present at measurement point $(x_k, y_j)$, and that remains at location $y_{N_y}$ to be sensed by the first optical system;

$w_{10}$ is the time-averaged power of the laser beam as sensed by the second optical system when no spray is present between the laser beam and the second optical system; and $w_1(x_{Nx}, y_j)$ is the time-averaged laser power obtained at location $x_{nx}$ when performing the $y_j$-profile characterization, as sensed by the second optical system.

3. The method as claimed in claim 1 where a first estimate of reception correction coefficients $C_{RX}(x_i, y_j)$, used in determining $N_D D_{20}^2$ is obtained by using the following expression:

$$C_{RX}(x_i, y_j) = \prod_{y_k=y_{N_y}}^{y_k=y_j+L_{SC}} \left(1 + \frac{\pi}{4} N_D D_{20}^2 \Delta y\right)_{(x_i, y_k)}, \quad C_{RX}(x_i, y_{N_y}) = 1,$$

applied in to successive $y_j$-profiles of the coordinate system contained in the measurement plane after knowing an estimation of the quantities $N_D D_{20}^2$ in the cartesian coordinate system y-profiles whose $y_k$ positions are closer to the first optical system than a particular $y_j$-profile that is being resolved, where:

$N_D$ is the spray particle density;

$D_{20}^2$ is the square of the spray averaged quadratic diameter constructed from the spatial spray number-size distribution probability density function $n_s(D)$ so that:

$$D_{20}^2 = \int_0^\infty n_s(D) D^2 dD$$

$\Delta y$ is the distance between consecutive y-profile characterizations; and $L_{sc}$ is proportional to the first optical system depth of field.

4. The method as claimed in claim 2 where a first estimate of the quantities $w_{sc}(x_k, y_j, y_j)/w_{10}$, used in determining $N_D D_{20}^2$ is obtained by using the following expression:

$$\frac{w_{sc}(x_i, y_j, y_j)}{w_{10}} = C_{RX}(x_i, y_i) \frac{w_{sc}(x_i, y_j, y_{N_y})}{w_{10}}$$

performed along $y_j$-profiles after determining the reception correction coefficients for a respective profile, where:

$w_{sc}(x_k, y_j, y_j)$ is an estimation of the time-averaged laser power scattered by the particles present at a measurement point $(x_k, y_j)$, as it would be sensed by the first optical system if no additional particles exist between the measurement point and the first optical system.

5. The method as claimed in claim 1 where a first estimate to the quantities $N_D D_{20}^2$ at measurement location $(x_i, y_j)$ is obtained by applying the following expression:

$$N_D D_{20}^2 \Big|_{(x_i, y_j)} = \frac{4}{\pi} \frac{1}{\tilde{K}} \frac{w_{sc}(x_i, y_j, y_j)/w_{10}}{1 - \frac{1}{\tilde{K}} \sum_{x_k=x_1}^{x_k=x_{i-1}} \frac{w_{sc}(x_k, y_j, y_j)}{w_{10}} \Delta x}$$

along $y_j$-profiles after determining the estimation of the quantities $w_{sc}(x_i, y_j, y_j)/w_{10}$ for a specific y-profile.

6. The method as defined in claim 4 where an updated estimation of $\underline{K}$ is obtained by inserting in the following expression:

$$\tilde{K} = \frac{1}{N_K} \sum_{j=kl}^{j=kl+N_K} K_j, \quad K_j = \frac{\sum_{x_k=x_1}^{x_k=x_{N_x}} \frac{w_{sc}(x_k, y_j, y_j)}{w_{10}} \Delta x}{1 - w_1(x_{N_x}, y_j)/w_{10}},$$

using the estimate of the $w_{sc}(x_i, y_j, y_j)/w_{10}$ quantities obtained before.

7. The method as claimed in claim 1, further comprising:
obtaining the tomographic map by means of the relative displacement between a spray generating injector and the first and second optical system used to capture the optical activity of the spray, in a plane coincident with the measurement plane, and sequentially positioning the object volume at a series of points in which the optical scattering and attenuation activity are registered.

8. An apparatus for the characterization of a polydispersed spray made of spherical particles said apparatus comprising:

a laser source which generates a laser beam made to coincide with an axis of a cartesian coordinate system contained in a measurement plane which intersects the spray;

a beam expander which converts the laser beam into a beam with a characteristic diameter greater than the maximum diameter of the particles present in the spray;

an optical element which directs the laser beam along a direction included in the measurement plane and coincident with the axis of the cartesian coordinate system defined in the measurement plane;

a first optical detector which detects scattering activity produced by the particles present in a probe volume located along a laser beam propagation direction and perpendicular to the laser beam propagation direction, said probe volume having a characteristic dimension greater than the maximum particle size present in the spray;

a first photodetector which converts the scattering activity incident upon the first optical detector into a first electrical signal;

a second optical detector which detects the radiation of the laser beam that remains after passing through the spray, the second optical detector filtering out laser radiation scattered by the particles;

a second photodetector which converts the radiation incident upon the second optical detector into a second electrical signal; and a processor which converts the first and second electrical signals output from the first and second optical detectors into a measure of the spray number density times the square of the quadratic average diameter of the spray present in each point of the cartesian coordinate system.

9. The apparatus as claimed in claim 8, wherein the first optical detector is disposed to receive laser radiation-scattered by the particles located in the probe volume and is localized in a small solid angle centered in the direction which is included in the measurement plane and forms a 90° angle with the laser beam propagation direction.

10. The apparatus as claimed in claim 9, wherein the first optical detector includes a receiver lens.

11. The apparatus as claimed in claim 10 wherein the first optical detector includes an aperture placed on an image plane of the receiver lens to receive optical information from the probe volume located along the laser propagation direction, said aperture being centered in the intersection of the laser propagation direction and the receiver lens, the aperture further being centered along the axis of the first optical detector, and normal to the measurement plane.

12. The apparatus as claimed in claim 8, where the second optical detector is located on an axis coincident with the propagation direction of the laser beam.

13. The apparatus as claimed in claim 12, where the second optical detector includes a receiver lens and an aperture located in a focal plane of the receiver lens, the aperture blocks all radiation impinging on the second optical detector that is not included in a cone whose axis is aligned with the propagation direction.

14. The apparatus as claimed in claim 8, where the first photodetector is comprised of a photomultiplier placed to receive light radiation exiting from the first optical detector, and the second photodetector is comprised of a photodiode placed to receive light radiation exiting from the second optical detector.

15. The apparatus as claimed in claim 14, further comprising an electronic amplifier coupled to the output of the photomultiplier, and to the output of the photodiode to obtain electrical signals proportional to light energy of the light radiation incident on the photomultiplier and photodiode.

16. The apparatus as claimed in claim 8, where an injector generates the spray and is mounted on a table or support that can be moved along two perpendicular directions contained in a plane parallel to the measurement plane.

17. The apparatus as claimed in claim 8, where the first optical system is mounted on a support that can be moved along two perpendicular directions contained in a plane parallel to the measurement plane.

18. The method for the characterization of sprays made of spherical particles as claimed in claim 1, where a spray volumetric flux in a given point $(X_i, Y_j)$ of the measurement grid is obtained from the expression:

$$q(x_i, y_j) = \frac{\pi}{6}(N_D D_{20}^2) \cdot \overline{DU}|_{(x_i, y_j)}$$

where $DU_{(X_i, Y_j)}$ is the velocity-size moment constructed from the following expression:

$$\overline{DU}|_{(x_i, y_j)} = \frac{\sum_k n_s(D_k) D_k^3 u(D_k)}{\sum_k n_s(D_k) D_k^2}$$

with $n_s(D_k)$ being the spatial number-size distribution of particles with diameter $D_k$ that characterizes an arbitrary particle size class $D_k$, and $u(D_k)$ is the average velocity perpendicular to the measurement plane of the said particle size class.

19. The method as claimed by claim 3, where a first estimate of the quantities $w_{sc}(x_i,y_j,y_j)/w_{10}$ are obtained by using the following expression:

$$\frac{w_{sc}(x_i, y_j, y_j)}{w_{10}} = C_{RX}(x_i, y_j) \cdot \frac{w_{sc}(x_i, y_j, y_{N_y})}{w_{10}},$$

along $y_j$ lines after determining the reception correction coefficients for that specific line;

a first estimate to the quantities $N_D D_{20\ x_i,y_j}^2$ is obtained by applying the following expression:

$$N_D D_{20_{x_i, y_j}}^2 = \frac{4}{\pi} \frac{1}{K} \frac{w_{sc}(x_i, y_j, y_j)/w_{10}}{1 - \frac{1}{K} \sum_{x_k=x_1}^{x_k=x_i-1} \frac{w_{sc}(x_k, y_j, y_j)}{w_{10}} \Delta x},$$

along $y_j$ lines after determining the estimation of the quantities $w_{sc}(x_i,y_j,y_j)/w_{10}$ for that specific line;

and upgraded estimations of $C_{RX}(x_i,y_j)$, $w_{sc}(x_i,y_j,y_j)/w_{10}$, and $N_D D_{20\ x,y_j}^2$ are obtained by repeating the above steps using the updated estimation of the averaged scattering constant K.

20. The method as defined by claim 19, where an updated estimation of K is obtained by inserting in the following expression:

$$\tilde{K} = \frac{1}{N_K} \sum_{j=kl}^{j=kl+N_K} K_j, \quad K_j = \frac{\sum_{x_k=x_1}^{x_k=x_{N_x}} \frac{w_{sc}(x_k, y_j, y_j)}{w_{10}} \Delta x}{1 - w_1(x_{N_x}, y_j)/w_{10}},$$

the estimate of the $w_{sc}(x_i,y_j,y_j)/w_{10}$ quantities obtained before;

and a repetitive cycle containing the steps defined above is followed to obtain more refined estimates of K, $C_{RX}(x_i,y_j)$, $w_{sc}(x_i,y_j,y_j)/w_{10}$, and $N_D D_{20\ x_i,y_j}^2$, until a number of repetitive cycles is completed or the absolute value of the difference between the averaged scattering constant K obtained after two consecutive cycles become smaller than a predefined percentage of its mean value in those consecutive cycles.

21. An apparatus for the characterization of a polydispersed spray made of spherical particles, said apparatus comprising:

a laser source which generates a laser beam made to coincide with an axis of a cartesian coordinate system contained in a measurement plane which intersects the spray;

an optical element which directs the laser beam along a direction included in the measurement plane and coincident with the axis of the cartesian coordinate system defined in the measurement plane;

a first optical detector which detects scattering activity produced by the particles present in a probe volume located along a laser beam propagation direction and perpendicular to the laser beam propagation direction;

a first photodetector which converts the scattering activity incident upon the first optical detector into a first electrical signal;

a second optical detector which detects the radiation of the laser beam that remains after passing through the spray;

a second photodetector which converts the radiation incident in the second optical detector into a second electrical signal; and a processor which processes the first and second electrical signals output from the first and second optical detectors to produce the characterization of the spray.

22. The apparatus as claimed in claim 21, further comprising:

a beam expander which converts the laser beam into a beam with a characteristic diameter greater than the maximum diameter of the particles present in the spray.

23. The apparatus as claimed in claim 21, wherein:

the first optical detector detects scattering activity produced by the particles present in a probe volume located along a laser beam propagation direction;

the probe volume is perpendicular to the laser beam propagation direction; and the probe volume has a characteristic dimension which is greater than the maximum particle size present in the spray.

24. The apparatus as claimed in claim 21, wherein the second optical detector detects further filters out laser radiation of the laser beam scattered by the particles.

25. The apparatus as claimed in claim 21, wherein the processor converts the first and second electrical signals output from the first and second optical detectors into a measure of the spray density multiplied by the square of the quadratic average diameter of the spray present in each point of the cartesian coordinate system.

* * * * *